United States Patent [19]

Fischer et al.

[11] Patent Number: 4,479,012
[45] Date of Patent: Oct. 23, 1984

[54] RECOVERY OF ALDEHYDES FROM HYDROFORMYLATION REACTION GAS

[75] Inventors: Karl Fischer, Worms; Armin V. Grenacher, Mutterstadt; Manfred Herr, Wachenheim; Max Strohmeyer, Limburgerhof, all of Fed. Rep. of Germany

[73] Assignee: BASF Aktiengesellschaft, Ludwigshafen, Fed. Rep. of Germany

[21] Appl. No.: 363,565

[22] Filed: Mar. 30, 1982

[30] Foreign Application Priority Data

Apr. 8, 1981 [DE] Fed. Rep. of Germany ....... 3114147

[51] Int. Cl.$^3$ .................... C07C 45/50; B01D 3/14
[52] U.S. Cl. .................... 568/454; 568/492; 203/87; 203/91; 203/98; 203/DIG. 6; 203/DIG. 19
[58] Field of Search ............ 568/451, 454, 492; 203/39, 98, 99, DIG. 19, 91, DIG. 6, 42, 87

[56] References Cited

U.S. PATENT DOCUMENTS

| | | | |
|---|---|---|---|
| 2,617,756 | 11/1952 | Eliot | 568/492 |
| 2,757,203 | 7/1956 | Hale | 568/451 |
| 2,821,559 | 6/1958 | Habeshaw et al. | 568/451 |
| 2,995,575 | 8/1961 | Schulz et al. | 568/451 |
| 3,092,670 | 6/1963 | Gwynn et al. | 568/451 |
| 3,501,531 | 3/1970 | Wilkinson | 568/451 |
| 3,791,935 | 2/1974 | Eubanks et al. | 203/99 |
| 4,210,426 | 7/1980 | Sridhar | 568/451 |
| 4,222,966 | 9/1980 | Bexten et al. | 568/451 |
| 4,287,369 | 9/1981 | Harris et al. | 568/454 |
| 4,299,990 | 11/1981 | Tummes et al. | 568/454 |

OTHER PUBLICATIONS

Chemical Engineering: Dec. 5, 1977, pp. 110-115.

*Primary Examiner*—Wilbur Bascomb
*Attorney, Agent, or Firm*—John H. Shurtleff

[57] ABSTRACT

Aldehydes are obtained from the gaseous product of the hydroformylation of olefinically unsaturated compounds using a rhodium catalyst by a process (cf. FIG. 2) in which
(a) this gaseous product is introduced, without being cooled or depressured, into a distillation column D,
(b) the top fraction from this column is cooled in a condenser K so that the greater part of the aldehydes contained therein is condensed,
(c) the condensate is separated, in a separator A, into a gas phase and a liquid phase,
(d) the gas phase from A, after waste gas has been separated off, is again brought to the hydroformylation pressure by means of a compressor P, and is returned to the reactor as a recycle gas,
(e) the liquid phase from A is returned to D, and
(f) the aldehydes are taken off from column D as liquid bottom products and/or as a vaporous side stream.

9 Claims, 2 Drawing Figures

CODE:
R = HYDROFORMYLATION REACTOR
K = CONDENSER
A = SEPARATOR
D = DISTILLATION COLUMN
E = DEGASSING COLUMN
P = COMPRESSOR
Q = GASEOUS PRODUCT STREAM

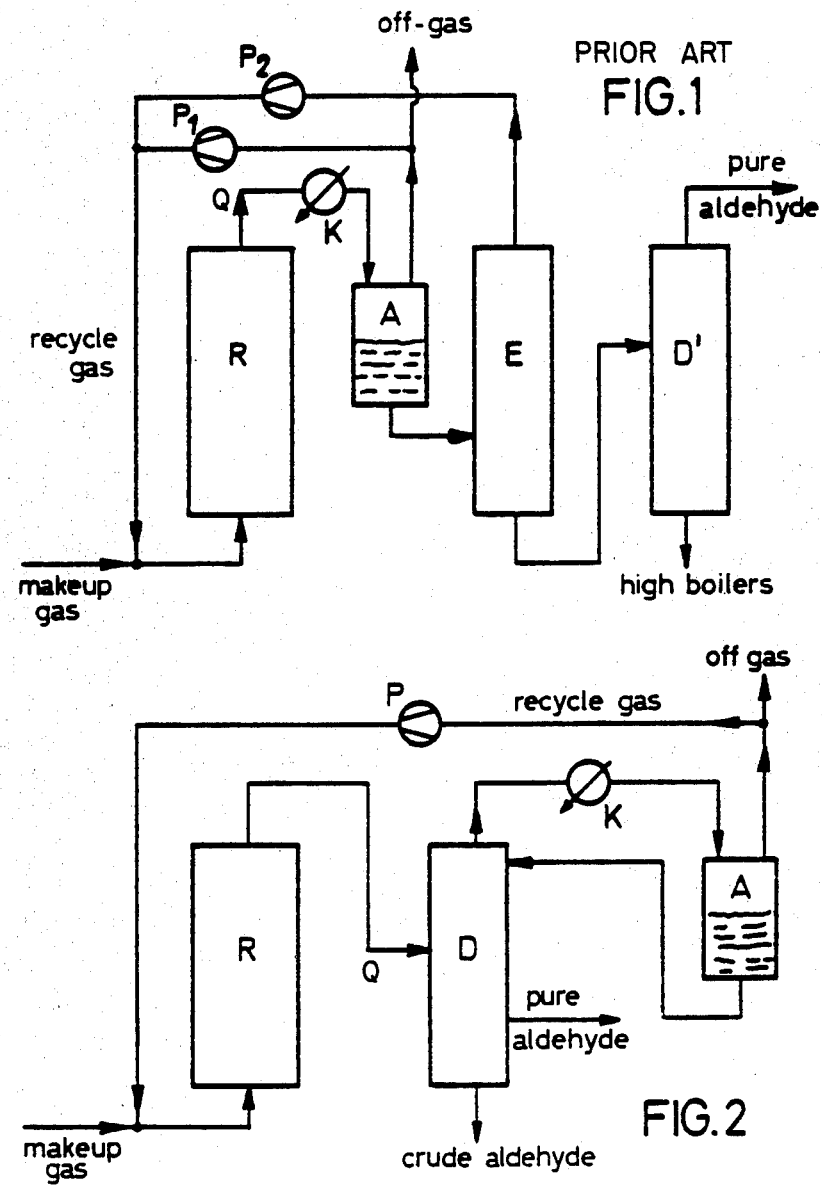

RECOVERY OF ALDEHYDES FROM HYDROFORMYLATION REACTION GAS

The present invention relates to an improved process for obtaining aldehydes which occur in vapor form, mixed with other reaction products and with unreacted starting materials, in the hydroformylation of olefinically unsaturated compounds using a rhodium catalyst.

The hydroformylation of olefinically unsaturated compounds using a rhodium catalyst is well known (cf. for example, Chemical Engineering, Dec. 5, 1977, page 110 et seq.) and therefore requires no further explanation, particularly since the invention relates to a process for obtaining the aldehydes from the hydroformylation mixture and not to the hydroformylation reaction itself.

BRIEF DESCRIPTION OF THE DRAWINGS

FIG. 1 is a flow diagram illustrating the conventional process for recovering aldehydes and FIG. 2 is a flow diagram illustrating the process of this invention for recovering aldehydes.

The aldehydes have hitherto been obtained in the following manner (cf. Chem.Eng. loc cit): the aldehydes are discharged from the reactor R (see FIG. 1) in vapor form, together with other gaseous constituents, and this gas mixture is cooled in condenser K so that a substantial part of the aldehydes is liquefied. This mixture is then separated, in a separator A, into a gas phase consisting of unreacted olefin, the corresponding paraffin, CO and $H_2$ on the one hand, and the liquid aldehyde phase on the other hand, after which the greater part of the gas phase is compressed and is returned to the hydroformylation stage as a recycle gas, fresh starting materials being added. A part of the recycle gas must be removed from the system as a waste gas in order that the amount of unusable gases, such as paraffin and nitrogen, does not increase continuously.

Since the liquid phase obtained in A still contains a substantial amount of dissolved olefin, this gas has to be expelled from the aldehyde phase by further heating in the degassing column E, in order to avoid olefin losses. The gases obtained in this procedure are compressed again and thereafter, as a recycle gas bleed stream, combined with the first-mentioned recycle gas stream, and are thus also returned to the synthesis stage. The liquid phase obtained in E is then worked up by a conventional distillation procedure, for example by separating it, in a column D', into the aldehyde fraction and the high-boiling bottom products, after which further working up steps may be carried out.

Apart from the pressure losses, which are compensated by the compressors $P_1$ and $P_2$, the system, including the degassing column E, is under the pressure chosen for the hydroformylation, ie. about 1–40 bars. The gases may be let down to atmospheric pressure downstream from column E, or at some other point in the further course of the process.

The disadvantage of this procedure is that the total amount of the crude aldehyde has first to be condensed by cooling and thereafter has to be reheated in the degassing column.

It is an object of the present invention to reduce the energy consumption resulting from the above procedure, and to simplify the apparatus used in obtaining the aldehydes.

We have found that this object is achieved by a process for obtaining aldehydes from the gaseous product of the hydroformylation of olefinically unsaturated compounds using a rhodium catalyst, wherein (a) this gaseous product is introduced, without being cooled or depressured, into a distillation column D,
(b) the top fraction from this column is cooled in a condenser K so that the greater part of the aldehydes contained therein is condensed,
(c) the condensate is separated, in a separator A, into a gas phase and a liquid phase,
(d) the gas phase from A, after waste gas has been separated off, is again brought to the hydroformylation pressure by means of a compressor P, and is returned to the reactor as a recycle gas,
(e) the liquid phase from A is returned to D, and
(f) the aldehydes are taken off from column D as liquid bottom products and/or as a vaporous side stream.

FIG. 2 illustrates the principle of this process, which, from the exit of the reactor to the stage of the degassed aldehyde, uses about 30% less energy than the prior procedure.

The novel process is useful for obtaining aldehydes whose partial pressures are high enough to make vaporous discharge worthwhile. This applies, in particular, to the production of propionaldehyde from ethylene and of butyraldehyde from propylene, and in general to the production of a $C_5$ aldehyde from the corresponding $C_4$ olefin. The process is particularly important for obtaining propionaldehyde and butyraldehydes.

The hydroformylation is carried out under the conventional pressure of about 1–40 bar, and accordingly all parts of the plant up to the point at which the product is discharged from column D are also virtually under this pressure. The unavoidable pressure loss as a result of line resistances is about 2 bar, and is compensated by the recycle gas compressor P.

The number of theoretical plates in column D is substantially independent of the type of the hydroformylation products, and is about 4–12. The temperature at the top of column D corresponds to the hydroformylation temperature, which is about 50°–140° C. in the case of the lower olefins.

The construction of column D is not critical, and as a rule a simple packed column is advantageously used.

Where ethylene and propylene are used, cooling the hydroformylation products to about 50°–70° C. is sufficient to condense them in condenser K.

The greater part of the gases, which comprise the olefinically unsaturated compounds, the corresponding saturated compounds and small amounts of other products, is returned as a recycle gas, via pump P, to the reactor. A small part of the gases, about 1–5% by volume, is removed from the system as a waste gas.

The crude aldehyde may be discharged from column D as a liquid bottom product, but it is particularly advantageous to discharge a part of the aldehyde (about 40–80%) as a vaporous sidestream of the pure aldehyde, the expense of further purification of the crude aldehyde being thereby reduced. Furthermore, it may be advantageous to discharge the total amount of crude aldehyde as a vaporous sidestream, so that only the high-boiling residues remain as the bottom product in column D. In other respects, the crude aldehyde may be purified further by conventional distillation.

EXAMPLE 15 kg/hour of ethylene were hydroformylated in a conventional manner in an experimental reactor R (see FIG. 2), using a rhodium catalyst at 110° C. under a pressure of 16 bars. The gaseous product, without being cooled or let down, was fed in at the level of the 6th tray of a packed column D which comprised a total of 8 theoretical plates, and was fractionated in this column.

The top fraction of column D was cooled in condenser K from 90° C. to 40° C., after which the liquid phase was separated, in separator A, from the gas phase, and was returned to the top of column D.

About 0.9 kg/hour of the gas phase, which essentially consisted of CO, $H_2$, ethylene and ethane, was discharged as a waste gas. The remaining part (about 31.1 kg/hour) was returned as a recycle gas via compressor P (pressure difference about 2 bar) to reactor R, fresh gas being added.

29.7 kg/hour of crude propionaldehyde were produced at the bottom of column D, at 153° C. This crude aldehyde still contained about 0.1% by weight of ethylene and about 1.1% by weight of a mixture of propanol and high-boiling by-products.

In a modified procedure, 19.1 kg/hour of propionaldehyde with a purity of 99.8% were taken off in vapor form at the level of the 2nd tray in column D. The residual amount of the product was obtained at 157° C. in the bottom of the column as the crude liquid aldehyde.

We claim:

1. In a process for recovering an aldehyde from the gaseous product obtained by the hydroformylation of an olefinically unsaturated compound in a reactor R at elevated temperature and pressure while using a rhodium catalyst, the improvement which comprises:
    (a) introducing said gaseous product, without being cooled or depressured, from the hydroformylation reactor R into a distillation column D for distillation in countercurrent with a liquid phase;
    (b) cooling the top fraction from said column D in a condenser K so that the greater part of the aldehyde contained therein is condensed;
    (c) separating the condensate in a separator A into a gas phase and a liquid phase;
    (d) separating off a portion of the gas phase from A as a waste gas, and then bringing the remaining portion of the gas phase from A to the hydroformylation pressure by means of a compressor P and returning it to the reactor R as a recycle gas;
    (e) returning the liquid phase from separator A to an upper part of the distillation column D to flow countercurrently with respect to the gaseous product; and
    (f) taking off the aldehyde from a lower part of column D.

2. A process as claimed in claim 1 which further comprises taking off the aldehyde from column D as a liquid bottoms product.

3. A process as claimed in claim 1 which further comprises taking off the aldehyde from column D as a vaporous side stream.

4. A process as claimed in claim 1 which further comprises taking off the aldehyde from column D in part as a liquid bottoms product and in part as a vaporous side stream.

5. A process as claimed in claim 1 wherein the olefinically unsaturated compound is a $C_2$- to $C_4$-olefin.

6. A process as claimed in claim 1 wherein the olefinically unsaturated compound is ethylene.

7. A process as claimed in claim 1 wherein the olefinically unsaturated compound is propylene.

8. A process as claimed in claim 5 carried out with a distillation column D of about 4 to 12 theoretical plates, the temperature at the top of said column D being about 50°–140° C., corresponding to the hydroformylation temperature.

9. A process as claimed in claim 8 wherein about 1–5% by volume of the recycled gas is withdrawn from the system as waste gas.

* * * * *